(12) United States Patent
Revkov et al.

(10) Patent No.: US 11,957,217 B2
(45) Date of Patent: Apr. 16, 2024

(54) METHOD OF MEASURING THE SHAPE AND DIMENSIONS OF HUMAN BODY PARTS

(71) Applicant: LIMITED LIABILITY COMPANY "FITTIN", Voronezh (RU)

(72) Inventors: Andrej Anatolevich Revkov, Voronezh (RU); Grigorij Vladimirovich Chujko, Voronezh (RU); Ivan Sergeevich Shedrin, Voronezh (RU); Egor Andreevich Revkov, Novosibirsk (RU); Natalja Demjanovna Grishko, Novosibirsk (RU); Viktor Valerevich Posmetev, Voronezh (RU); Dmitry Mikhailovich Kanin, Selo Jamnoe (RU)

(73) Assignee: LIMITED LIABILITY COMPANY "FITTIN", Voronezh (RU)

( * ) Notice: Subject to any disclaimer, the term of this patent is extended or adjusted under 35 U.S.C. 154(b) by 0 days.

(21) Appl. No.: 17/043,151

(22) PCT Filed: Apr. 3, 2019

(86) PCT No.: PCT/RU2019/050041
§ 371 (c)(1),
(2) Date: Sep. 29, 2020

(87) PCT Pub. No.: WO2019/194707
PCT Pub. Date: Oct. 10, 2019

(65) Prior Publication Data
US 2021/0145127 A1    May 20, 2021

(30) Foreign Application Priority Data
Apr. 3, 2018   (RU) ............................ RU2018111932

(51) Int. Cl.
*A43D 1/02* (2006.01)
*A61B 5/107* (2006.01)
(Continued)

(52) U.S. Cl.
CPC .............. *A43D 1/025* (2013.01); *A43D 1/027* (2013.01); *G06T 7/0012* (2013.01); *G06T 7/13* (2017.01);
(Continued)

(58) Field of Classification Search
CPC ...... A43D 1/025; A43D 1/027; A43D 999/00; A43D 1/02; A61B 5/1079; A61B 5/1074;
(Continued)

(56) References Cited

U.S. PATENT DOCUMENTS

| | | | |
|---|---|---|---|
| 2003/0103682 A1* | 6/2003 | Blake | ...................... G06T 7/143 |
| | | | 382/199 |
| 2010/0111370 A1* | 5/2010 | Black | .................. G06Q 30/0601 |
| | | | 705/26.1 |

(Continued)

FOREIGN PATENT DOCUMENTS

| | | |
|---|---|---|
| RU | 2034509 C1 | 5/1995 |
| WO | 2018007384 A1 | 1/2018 |

OTHER PUBLICATIONS

Yang et al. "A Charged Geometric Model for Active Contours." 18th International Conference on Pattern Recognition, Aug. 20, 2006, 4 pages (Year: 2006).*

*Primary Examiner* — Jon Chang
(74) *Attorney, Agent, or Firm* — Nadya Reingand

(57) ABSTRACT

This invention belongs to measurement methods that can be used in light industry, when measuring the shape and size of the human body parts. Disclosed is a method, over the course of which, based on a series of photographs an image of a flat object of known shape and size is identified on each (Continued)

photograph. The body part area is isolated from the background in the image, and the area of an arbitrary body that does not belong to the projection of the human body part is cut out. Also disclosed is a method for searching an image of a flat object of known shape and size, its projection, and the camera location and orientation, over the course of which the predicted image of the flat object is compared to the real on. Here, the particle dynamics technique is used for isolating a human body part from the image background.

11 Claims, 11 Drawing Sheets

(51) Int. Cl.
*G06T 7/00* (2017.01)
*G06T 7/12* (2017.01)
*G06T 7/13* (2017.01)
*G06T 7/564* (2017.01)
*G06T 7/62* (2017.01)
*G06T 17/00* (2006.01)

(52) U.S. Cl.
CPC .............. *G06T 7/564* (2017.01); *G06T 17/00* (2013.01); *A43D 1/02* (2013.01); *A61B 5/1074* (2013.01); *A61B 5/1079* (2013.01); *G06T 7/12* (2017.01); *G06T 7/62* (2017.01)

(58) Field of Classification Search
CPC ......... G06T 7/0012; G06T 7/13; G06T 7/564; G06T 17/00; G06T 2207/10016; G06T 7/12; G06T 2207/30196; G06T 2207/30244; G06T 7/62; G06T 7/75
See application file for complete search history.

(56) References Cited

U.S. PATENT DOCUMENTS

2016/0286906 A1   10/2016  Malal et al.
2019/0028637 A1*   1/2019  Kolesov ................ H04N 23/63

* cited by examiner

METHOD OF MEASURING THE SHAPE AND DIMENSIONS OF HUMAN BODY PARTS

CROSS-REFERENCE TO RELATED APPLICATIONS

The present patent application is the National stage application from the PCT application PCT/RU2019/050041 filed Apr. 3, 2019 which claims priority to Russian patent application RU 2018111932 filed Apr. 3, 2018.

FIELD OF INVENTION

This invention falls into the category of measurement methods and can be used in light industry, especially in the footwear and garment industries, when measuring the shape and size of parts of human body. It can also be used in orthopedics and makes it possible to perform remote diagnosis of foot deformities (diseases), particularly, flat-footedness.

The method can be used in everyday life and in the trading industry during the marketing, sale, and remote purchase of apparel and footwear that fit the real features of the customer's body. It can also be used for virtual footwear fitting at Internet stores or in mobile applications for remotely purchasing footwear and ordering handmade footwear.

BACKGROUND

A known foot measurement method [US 20170053335 A1] entails acquiring a three-dimensional image of a foot and comparing it to an extensive database of stored footwear information. This method makes it possible to determine the size better than conventional systems, wherein a smartphone/iPhone/digital camera and related interface tools suggest the best choice of a footwear option from multiple offers.

The shortcomings of this method consist of low accuracy, a narrow area of application (the method does not work when heavy shadows, glares, and poor lighting are present), high labor intensity, and lengthy footwear selection time.

A method for the contactless measurement of the foot surface [RU2034509, May 10, 1995] is the one closest to the engineering solution at hand. This method consists of placing the foot on a base platform, illuminating the foot surface with sheet light beams, and obtaining an image of the trace of these beams for the outer and inner side surfaces of the foot separately using two video cameras, the optical axes of which are oriented at acute angles relative to the reference plane and the sheet beams. The foot is aligned by the video cameras, which are turned toward the heel of the foot. Here, an angle forms between the projection of the optical axes of the video cameras onto the reference plane. This angle's vertex is oriented toward the heel of the foot and occupies a point located along the projection of the angle's bisector between the optical axes of the cameras on the reference plane. Using a heel stop, the heel of the foot is aligned with a predetermined reference point located along the projection of the angle's bisector.

The shortcomings of this prototype method include poor accuracy, high labor intensity, and lengthy footwear selection time.

SUMMARY

The technical result of the group of inventions at hand is increased accuracy.

This technical result is achieved by using the method for measuring the shape and size of parts of human body, over the course of which, based on a series of photographs obtained from different aspect angles of the part human body, an image of a flat object of known shape and size is identified on each photograph, by means of which the camera position and orientation are determined, the body part area is isolated from the background in the image, and the area of an arbitrary body that does not belong to the projection of the part of human body is gradually cut out of the arbitrary body that initially included the part of human body on each frame.

The aforementioned method entails the use of the method for searching an image of a flat object of known shape and size, its projection, and the camera location and orientation, over the course of which the camera position and orientation parameters are repeatedly reset in a random manner, and the predicted image of the flat object of known shape and size is compared to the real one using a template that consists of several rows of points along the contour of the flat object of known shape and size, between the points of the inner and outer rows of which the difference in brightness is computed pairwise in order to calculate the match criterion.

The foregoing method also entails the use of the method for isolating a part of human body from the background in an image, over the course of which the particle dynamics technique is employed, within which the boundary between the body part area and the background is presented in the form of a set of points sequentially located so as to form a contour, moving under the action of conditional forces that preserve the connectivity of the contour, and tending to move a point to a place of a significant change in brightness, thereby forming a closed contour that circumscribes the simply connected body part area.

Thus, these methods are intended to be used together.

DETAILED DESCRIPTION OF THE PREFERRED EMBODIMENT

The utilization of this invention will lead to a decrease in labor intensity, as well as part of human body shape and size measurement time, and an expanded opportunity for its use on groups of people with limited mobility: infants and the elderly.

The method's use makes it possible to generate a 3D model, for example, of a leg (the foot and the lower leg) by means of processing a series of photographs obtained while passing a device with a video camera around the foot—increased accuracy, a decrease in labor intensity and measurement time, and the expansion of the area of application by virtue of the ability to use it in conjunction with mobile devices. The subject method is ideally suited for virtual fitting, since it is convenient for users, in addition to which it does not require the presence of special equipment, software, or the transfer of a large volume of data.

At the present time, the process of the 3D scanning of objects using professional 3D scanners is based on the additive principle; i.e., everything that a scanner sees is then included in the 3D model. For this reason, scanning consists of two steps: object scanning and subsequent manual 3D model processing, during which it is necessary to eliminate the debris and residue of the surface on which the object is standing or is being held, and to properly mend the holes. Because this step is not presently automated in any way, the human factor plays a major role, which means that there is a high likelihood of human errors.

This method, firstly, is based on the inverse principle, everything that a scanner captures is excluded from the final voxel model, and secondly, it automates all the steps, minimizes errors, and reduces noise during all the steps, in addition to which verification operations exist for ensuring the best object accuracy.

Figure 1:
FIG. 1 shows a 3D model of a foot that was obtained using a professional Sense 3D scanner, which has a stated accuracy on the order of 1 mm.
Figure 2:
FIG. 2 shows a final voxel model obtained by scanning with our technique.
Figure 3:
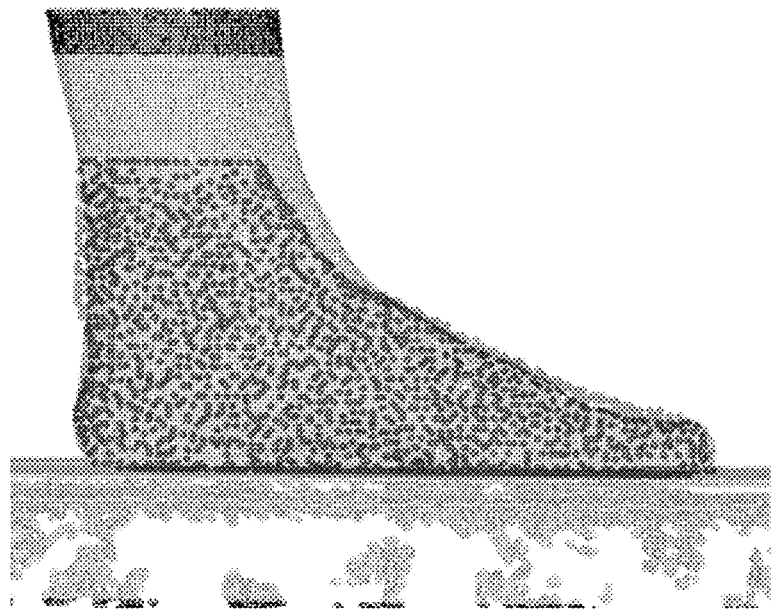
FIG. 3 shows comparison of two 3D models.

Scanning with a conventional 3D scanner results in obtaining a model with a multitude of noises. FIG. 1 shows a 3D model of a foot that was obtained using a professional Sense 3D scanner, which has a stated accuracy on the order of 1 mm. Next, in FIG. 2, a final voxel model obtained by scanning with our technique is depicted. A comparison of these two 3D models, which is presented in FIG. 3, confirms the high accuracy of our technique. Another advantage of the method under consideration consists of the fact that a solid-state model is ultimately obtained, as opposed to the polygonal model produced by scanning with a professional Sense 3D scanner.

The embodiment of the invention is explained by the following examples.

Example 1

1. Preparation for Scanning

Prior to the start of scanning, it is necessary to ensure conditions that are sufficient for obtaining the highest quality three-dimensional model of the foot. In particular:

uniform lighting, without bright directional light, shadows, or glares;

the floor color must be a contrast of white, monochromatic, and necessarily hard (when scanning on a carpet with a high pile, the corners of the A4 sheet are raised, which does not make it possible to accurately determine the A4 sheet coordinates)

the foot should be clad in a dark sock (preferably black), so it is isolated from the rest of the background as a connected dark domain 2. The Scanning Step (Obtaining a Series of Photographs)

Figure 4:
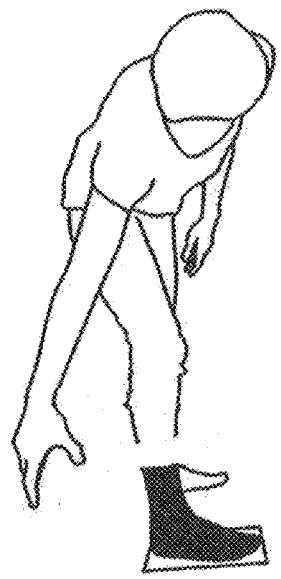
FIGS. 4 and 5 show examples of scanning process using a smartphone.
Figure 5:
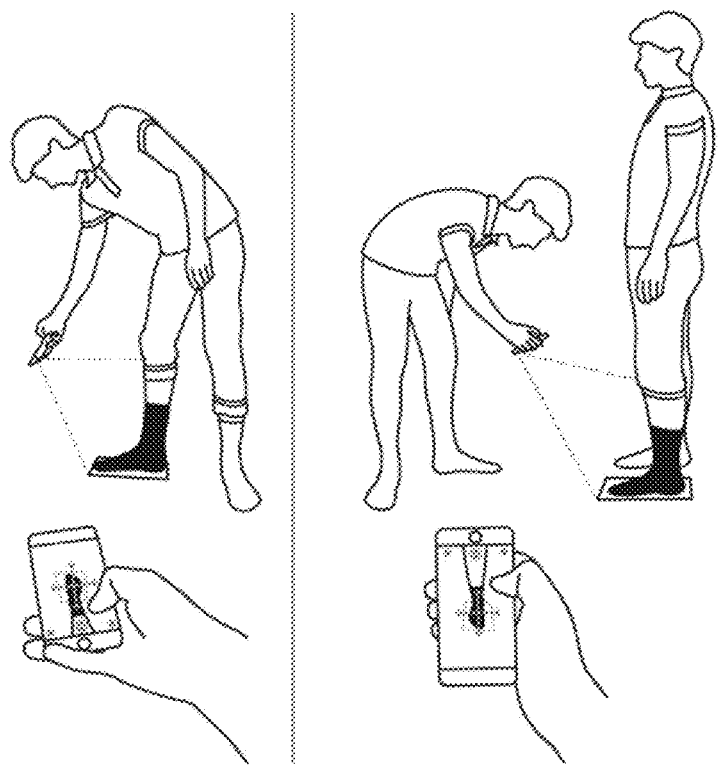

In order to generate a three-dimensional model of a foot, it is necessary to place the foot in the middle of a sheet of white A4 paper, line the heel up with the edge of the sheet, lean on the foot, and pass a device with a video camera (a smartphone or a web camera connected to a personal computer or laptop) around the foot in an arc of about 200° from one side of the body to the other. It is desirable to perform foot contouring from the knee level in order to achieve the best 3D model accuracy; however, the method is still efficient when the height of device movement is 10 cm or more from the floor. Upon the commencement of scanning, the user presses the START button, the smartphone's camera is activated for recording, and one frame per second is saved from the video stream, with the scanning process ending when the DONE button is pressed. The scanning process using a smartphone is examined in FIGS. 4 and 5.

It is understood that the A4 sheet must be fully visible in each photograph. The lower leg must be visible in the photographs in order to determine lower leg shape and size. The condition must also be met that at least two pixels fall within one millimeter of the scene shown in the photograph. For example, for a 5-megapixel camera, this is achieved if the length of the A4 sheet in a photograph is not less than ⅓ of the length of the photograph.

3. Creating of a Series of Photographs

Figure 6:
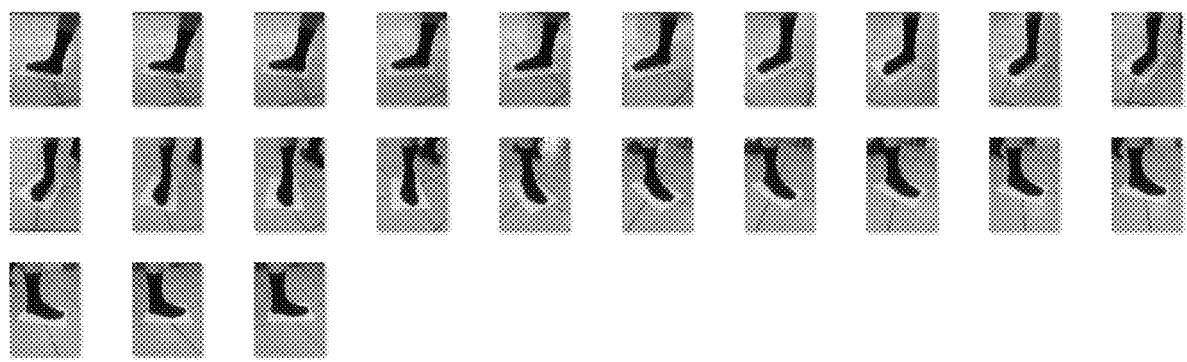
FIG. 6 shows the rephotograph on a mobile device.

As a result of scanning, a series of photographs is obtained in the resolution set on the mobile device (at least 2, the maximum number is unlimited, the optimal number is 12). An example of photographs of this type is presented in FIG. 6.

In order to achieve maximum three-dimensional model quality and a high processing speed, it is advisable to keep 12 photographs from the entire set, selected as the sharpest and evenly distributed throughout the set.

4. Reducing and Cropping the Photographs

For the purpose of ensuring identical (predictable) photograph processing conditions and decreasing outgoing traffic when transferring photographs from a smartphone to a server, all the photographs are reduced by an integer number of times that is multiple of 2, so that the resolution is at least 480×640. Photographs larger than this resolution are cropped down to it, so the A4 sheet is located in the center of a photograph. At the output, we obtain a series of photographs with a resolution of 480×640.

5. The A4 Sheet Contour is Determined on Each Photograph

By gradually increasing the image contrast with a shift in the average level, after 10-20 iterations, the light areas become white, the dark areas become black, and the border remains in its place. The shadows disappear and blurred borders turn into sharp ones.

Figure 7:
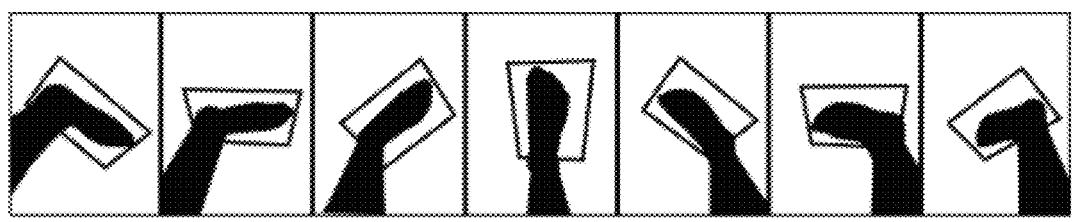
FIG. 7 demonstrates using Monte Carlo Technique to search for A4 sheet.

The Monte Carlo technique is used to search for the A4 sheet. A set of photographs with a detected A4 sheet contour is examined in FIG. 7.

Figure 8:
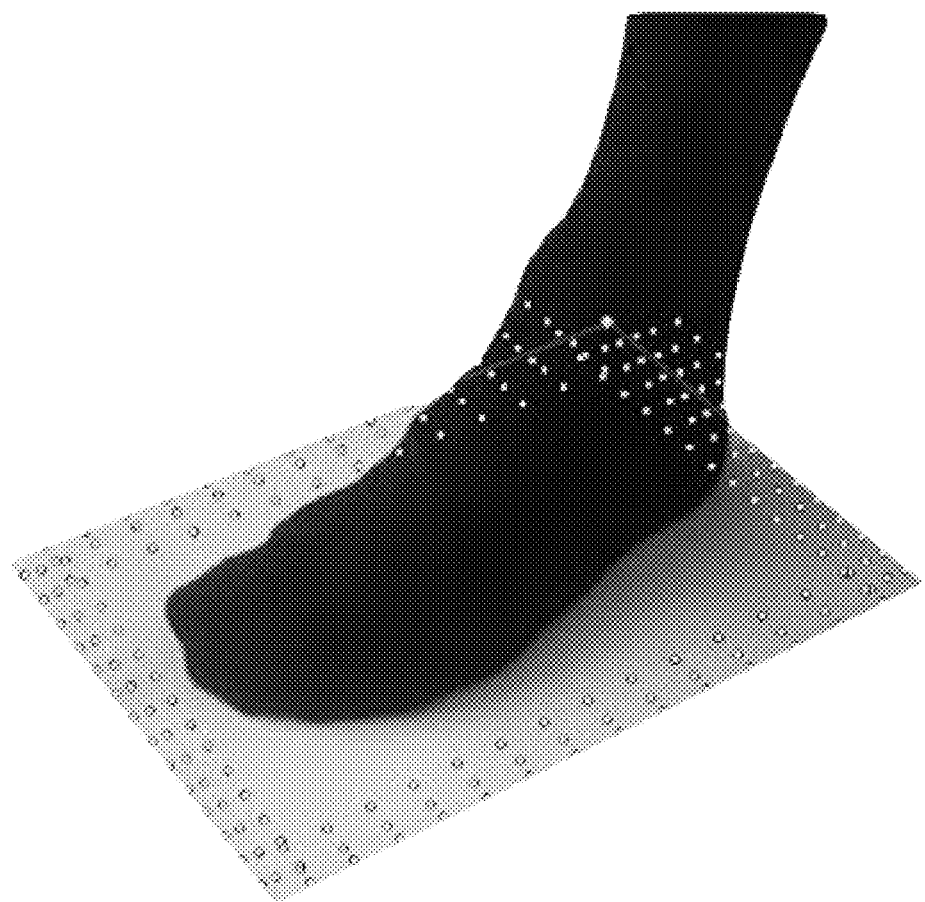
FIG. 8 shows a template that was used to verify the match of the predicted A4 sheet image with the real one.

The template shown in FIG. 8 is used to verify the match of the predicted A4 sheet image with the real one, which takes the form of rows of points parallel to each edge of the sheet. The number of rows is 2 or higher, the optimal number is 6 rows, the number of points per row is 4 or higher, and the optimal number is 20-40. The optimization criterion for checking the match consists of the differences in intensity at the paired points of the corresponding series, taken with certain weighting coefficients.

The gradual narrowing of the desired camera parameter ranges is used to hasten the Monte Carlo technique convergence. The number of elementary checks for finding an A4 sheet with an acceptable accuracy comes to on the order of $10^5$-$10^6$.

Figure 9:
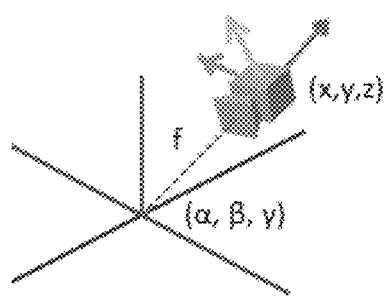
FIG. 9 illustrates the determination of camera position and orientation.

6. The Camera Position and Orientation are Determined as a Function of the A4 Sheet Position The task of determining the camera parameters (the x, y, and z coordinates in space, the camera orientation angles, α, β, and γ, and the focal length, f) is posed as the inverse: it is necessary to select the camera parameters in such a manner that the predicted image of the A4 sheet matches the real one in a photograph to the greatest extent possible. An illustration that explains the determination of camera position and orientation is presented in FIG. 9.

The camera parameters found are then used to cut the 3D model from the voxel array.

7. The closed contour of the foot and the lower leg between the dark sock and the light A4 sheet and the background is distinguished in each photograph using the evolutionary technique.

Figure 10:
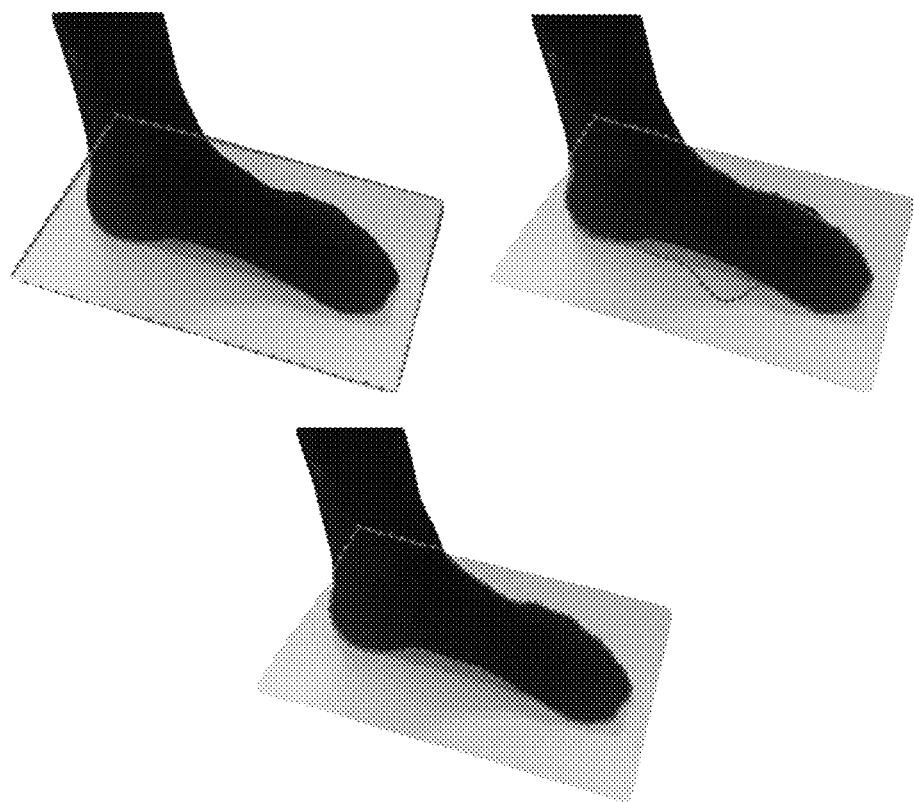
FIG. 10 shows the result of foot contour isolation.

The closed contour of the foot and the lower leg is sought using a particle dynamics technique that is adaptable to the subject area. This technique consists of the fact that when the contour is pulled onto the foot area, the points are initially located on the edges of the A4 sheet, and the "physical interaction" and "mechanical movement" of the points are calculated. The conditional attractive forces acting between adjacent points lead to drawing of points towards the foot while keeping the distances between the points roughly constant. A force proportional to the numerical estimation of the second derivative of photograph intensity across the contour is added in order to find the foot contour. To this end, the intensity is read from the paired points inside and outside the contour, distributed relative to the contour (by analogy with the A4 sheet search step). The result of foot contour isolation from the background is shown in FIG. 10.

Figure 11:
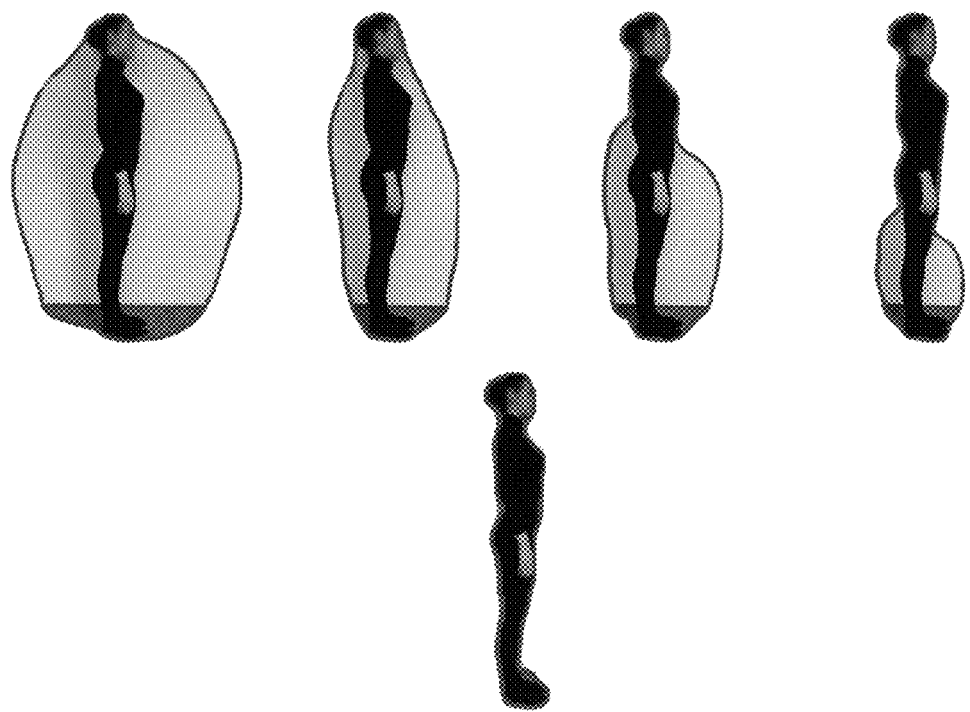
FIG. 11 demonstrates the use of this technique to isolate a human contour.
Figure 12:
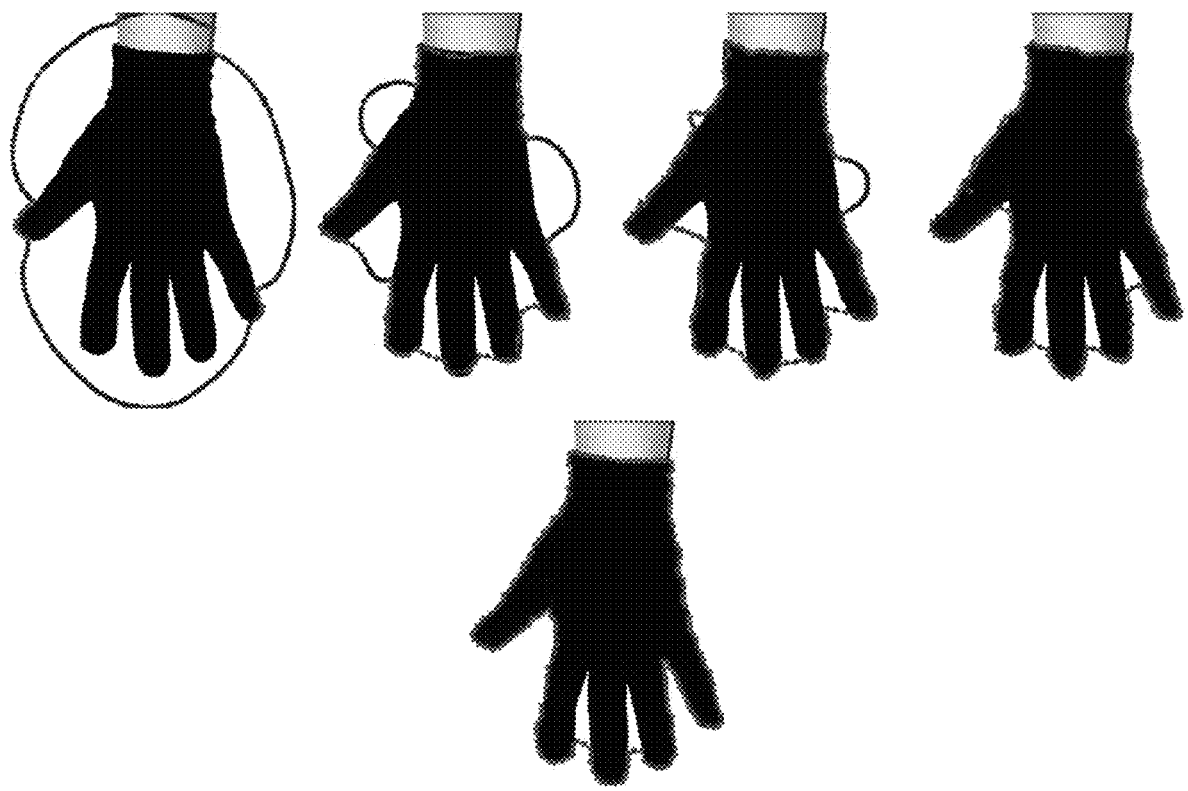
FIG. 12 demonstrates the use of the technique to isolate a contour of the human hand.

FIG. 11 demonstrates the use of this technique to isolate a human contour. FIG. 12 demonstrates the use of the technique to isolate a contour of the human hand.

Contour accuracy is additionally checked via the following sequence of actions:
the image is converted to gray,
a median filter is used for smoothing,
a Canny boundary detector (a Canny filter) is then applied,
the image brightness gradient at each point is calculated using the Sobel operator.

Figure 13:
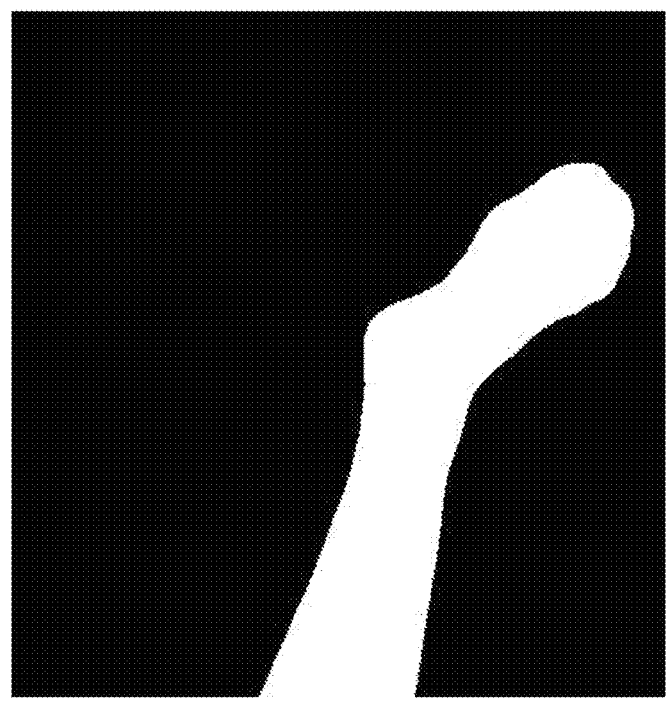
FIG. 13 shows the result of the actions for checking the contour accuracy.
Figure 14:
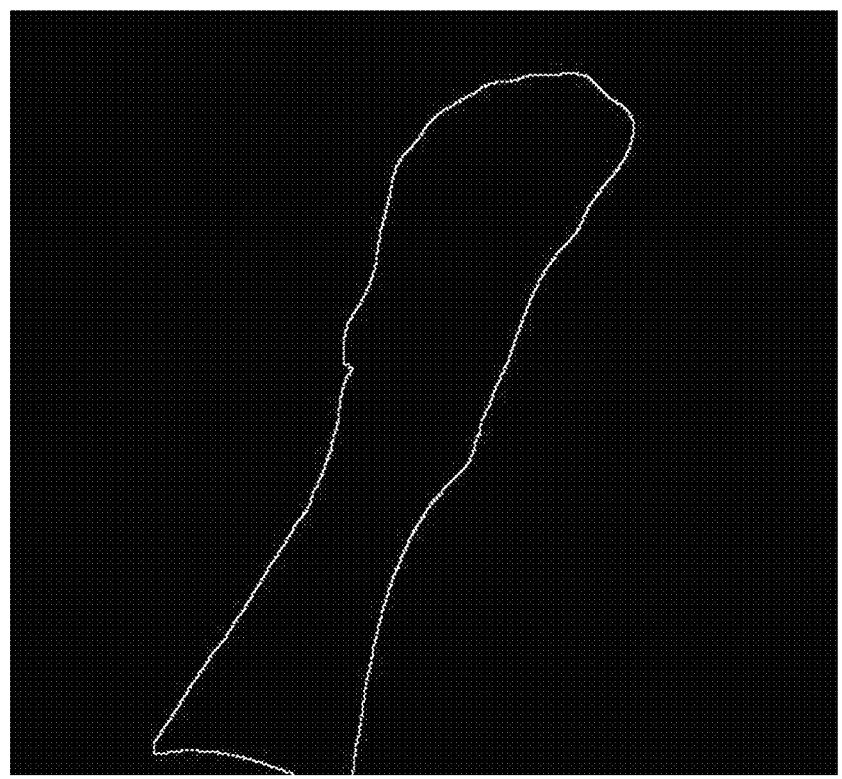
FIG. 14 shows improved contour accuracy.

The result of these actions is depicted in FIG. 13. From this fill, we then obtain the contour that is shown in FIG. 14.

Figure 15:
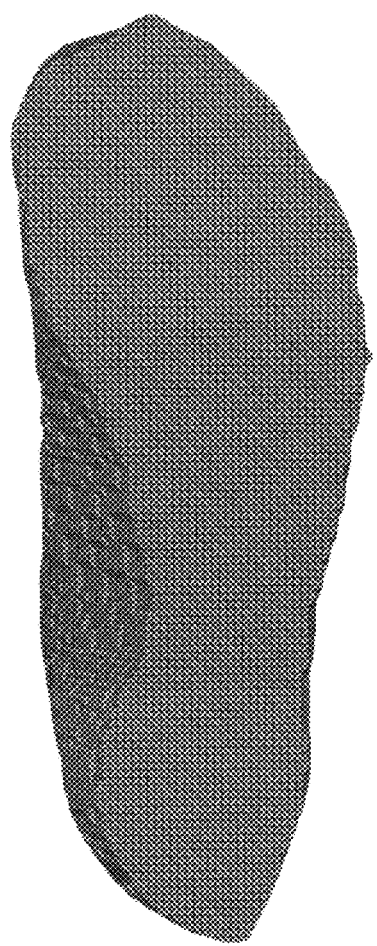
FIGS. 15 and 16 shows a 3D model of a foot with a well-defined foot arch.
Figure 16:
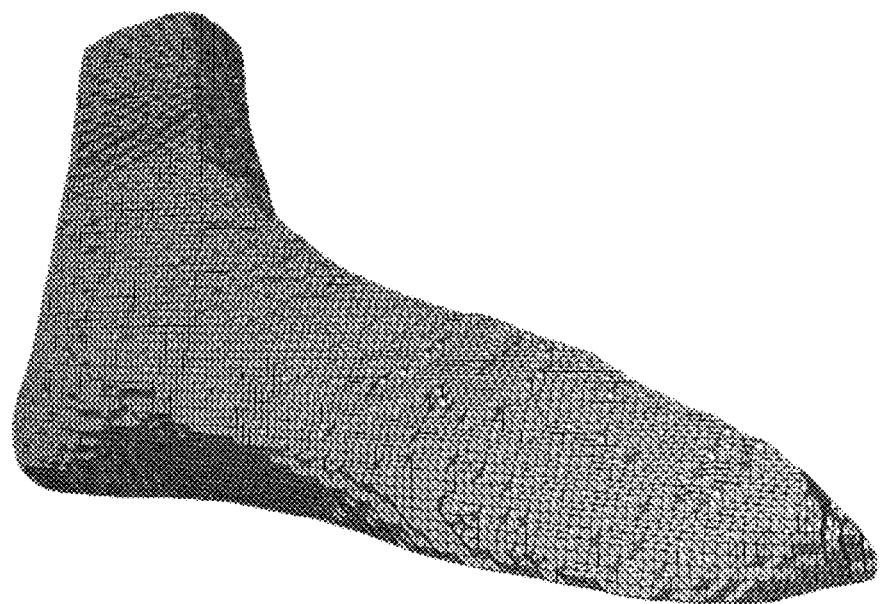

The subject contour construction technique makes it possible to determine the foot arch height, which must be taken into account during the selection of footwear for people with flat feet. With most lighting options, a shadow is present in the image near this area. The algorithm developed makes it possible to isolate the dark connected area of the foot from the shadow, with the exception of instances of a very strong or smoothly transitioning shadow, when it is difficult, to isolate the shadow from the surface of the foot even for a person using a visual apparatus. A 3D model of a foot with a well-defined foot arch is examined in FIGS. 15 and 16.

Figure 17:
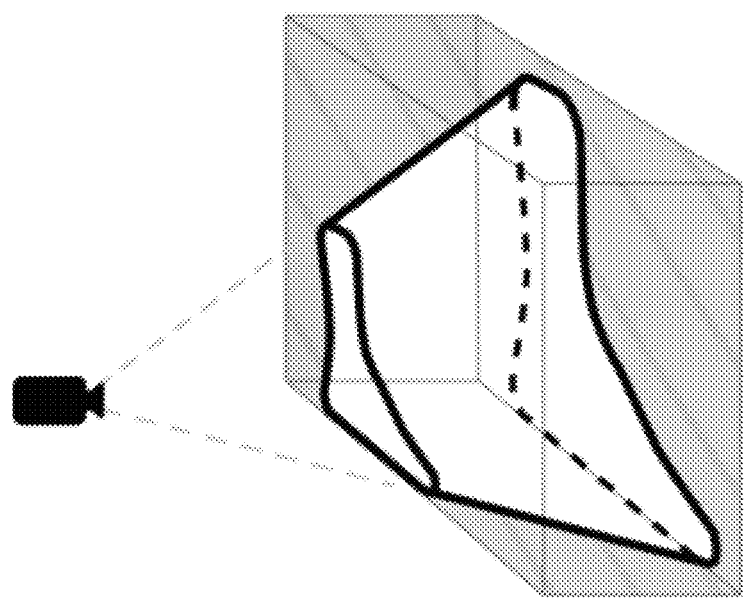
FIG. 17 shows the foot contour.

8. With each frame, from the voxel array, which is initially parallelepiped-shaped and is located above the A4 sheet, voxels are cut off outside the space bounded by a conical secant surface with its vertex located at the camera and its directrix being the foot contour obtained during the previous step, as depicted in FIG. 17.

Figure 18:
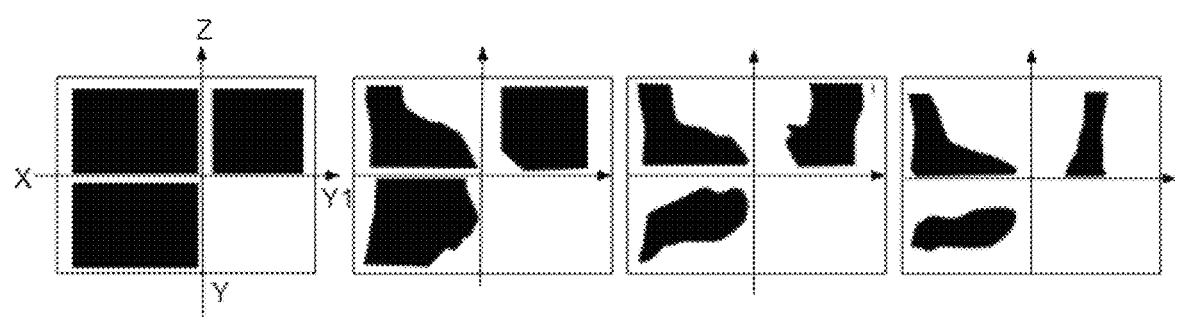
FIG. 18 shows the foot voxel model creation sequence.
Figure 19:
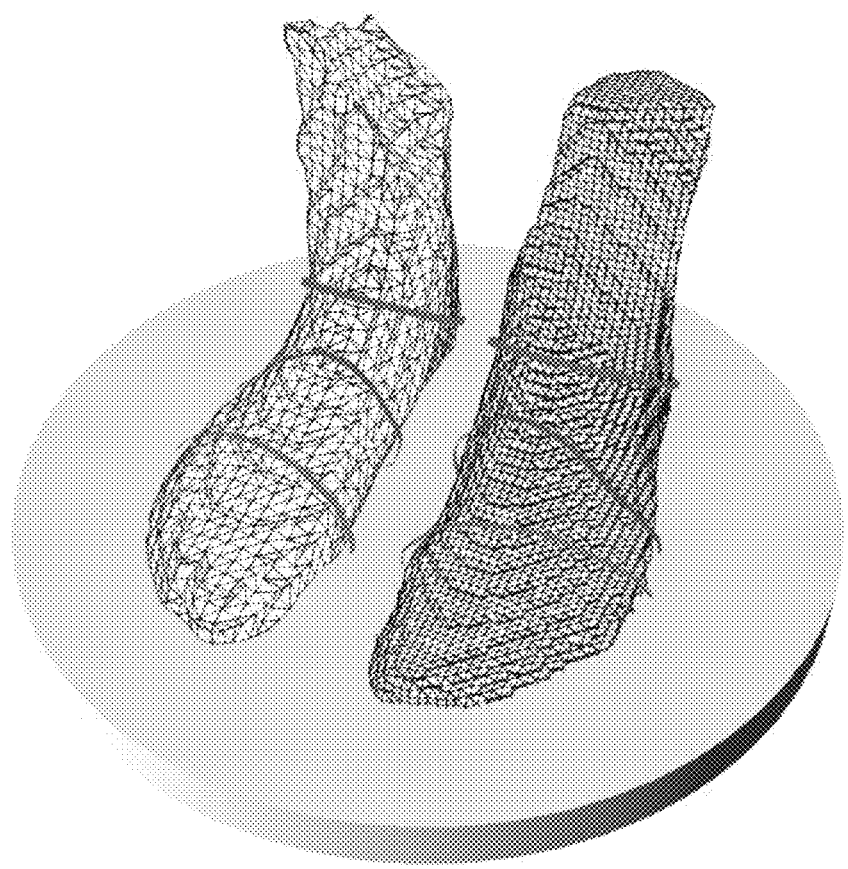
FIG. 19 shows a 3D model of the foot: the right foot—a voxel representation, the left foot—a Polygonal representation.

Each frame makes it possible to cut the projection of the previously found foot contour from the initial monolithic voxel array. As the voxel model is gradually cut from different aspect angles, a sufficiently accurate 3D voxel model of the foot is created. The foot voxel model creation sequence is presented in FIG. 18. Three projections of the initial voxel array are shown on the left. Three projections of the resultant foot voxel model are shown on the right. Voxel and polygonal representations (without additional smoothing and grid regularization) of a 3D model of the foot are examined in FIG. 19 (the right foot—a voxel representation, the left foot—a polygonal representation).

9. A scanning artifact in the form of a peculiar "comb" is eliminated from the resultant voxel model.

In order to simplify and speed up the scanning procedure, the camera is guided in a smooth arc at knee height. Here, the area above the foot (the "bridge") is less accurately defined than the other parts of the foot due to the fact that when the voxel array is cut from these optical directions by the leg contour projections above the foot, an incompletely cut area is created—a "comb", which represents an area of the model with a sharp upper edge, as a result of which 3D foot model parameters such as "height in lift" and "lift-heel girth" are overestimated.

Therefore, an algorithm for correcting the upper surface of the foot is used during the next step.

Figure 20:
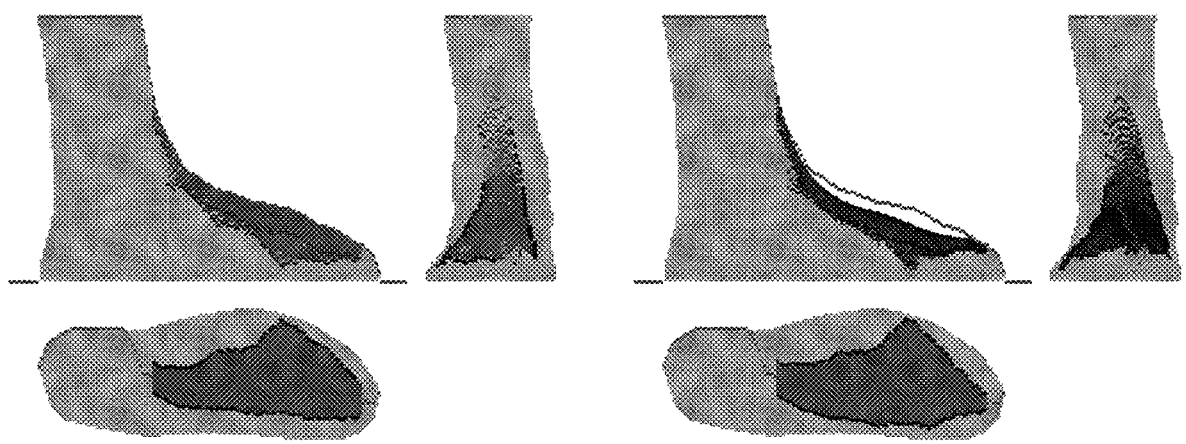
FIG. 20 shows three projections of a voxel model with a "comb" being examined on the left, while three projections of a voxel model following "comb" removal being examined on the right.
Figure 21:
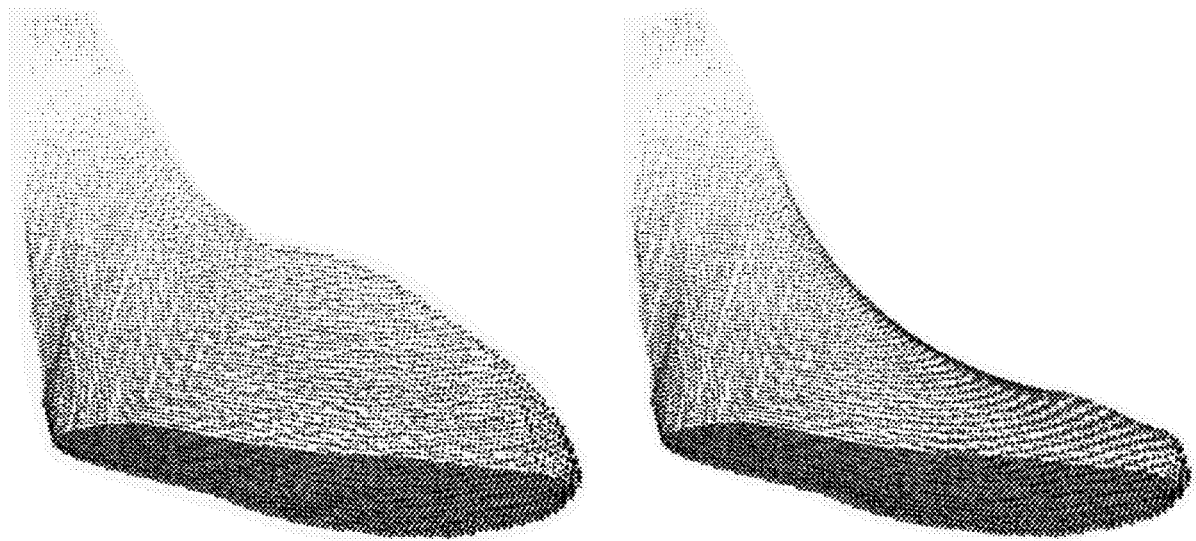
FIG. 21 shows two voxel models with a "comb" and without a "comb".

A special algorithm based on the interacting moving point technique is used to eliminate the "comb". To this end, the surface area above the foot, which must be corrected, is isolated beforehand. During the evolutionary cycle, the mechanical interaction and the movement of the surface points are then calculated. Information about the shape of the foot from the sides is used to facilitate the soundest restoration of the surface above the foot. Two types of forces act between the moving points: attractive forces, which tend to shorten the distance between the points to the greatest extent possible, and bending reduction forces, which tend to make the surface as smooth as possible. In FIG. 20, three projections of a voxel model with a "comb" are examined on the left, while three projections of a voxel model following "comb" removal are examined on the right. Two voxel models with a "comb" and without a "comb" are presented in FIG. 21.

The comb correction algorithm is not required if more thorough leg scanning is performed, capturing "side views" on the left and right, for example, if the camera guidance arc does not proceed from the knee height, but rather begins at the supporting surface to the right of the leg, rises to the knee level when viewed from the front of the leg, and descends again to the supporting surface to the left of the leg.

10. The 3D model is converted from the voxel format to obj format—for subsequent viewing and storage in a compact form. In this instance, the model is additionally smoothed and grid regularization is performed.

Over the course of processing, a leg area space filling field is created beforehand, then the key points are located on the outer surface of the field (the maximal gradient region) based on the maximization of surface coverage uniformity, then they are connected by means of ribs. Using the field approach, the model is smoothed; the smoothing level is regulated by a special parameter during the creation of the field. Using the set of points and ribs consequently obtained, triangles are constructed, and this data set is converted to the "obj" format.

Figure 22:
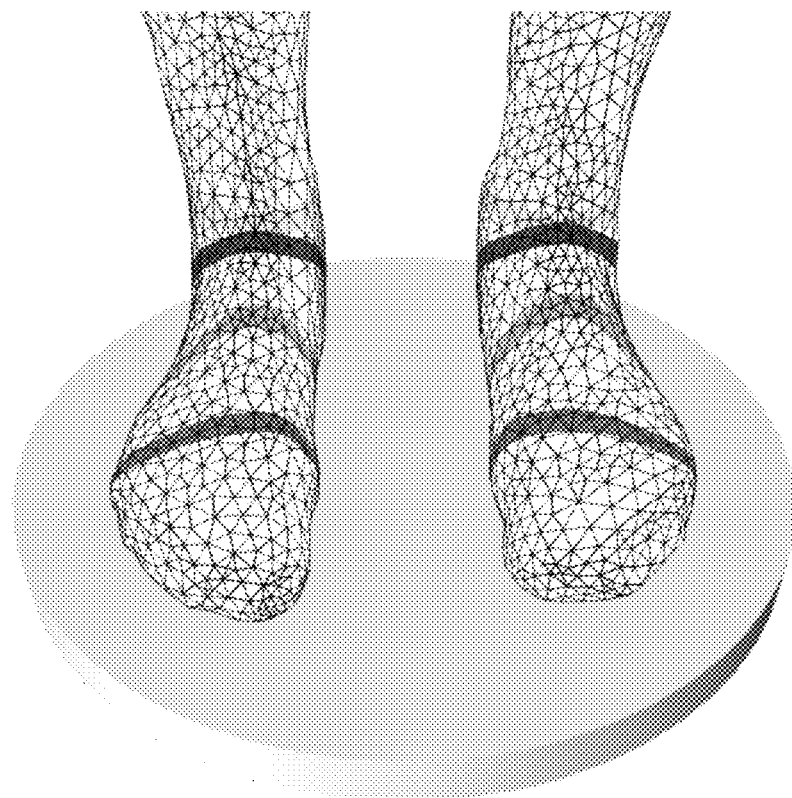
FIG. 22 shows two accurate polygonal 3D models of human legs.

Two accurate polygonal 3D models of human legs are presented in FIG. 22, which were obtained in a contactless manner by passing a device with a video camera around the leg in an arc from knee level from one side of the body to the other.

What is claimed is:

1. A method for measuring a shape and a size of a human body part, comprising recording a series of photographs taken from different angles of the human body part;
   identifying an image of a flat object of a known shape and size on each photograph based on the series of photographs taken from the different angles of the human body part;
   using the identified image of the flat object to determine a position and an orientation of a camera;
   providing a template for the flat object of the known shape and size, including several rows of points along a contour of the flat object;
   isolating an area of the human body part from a background in the image and gradually removing an area of any arbitrary body that does not belong to a projection of the human body part, with frames allowing the projection of a previously found contour of the human body part to be removed from a monolithic voxel array, wherein a particle dynamics method is used to extract the human body part from the background in the image, a boundary between an area of the human body part and the background is represented by a set of sequentially arranged points that form the contour moving under an influence of conditional forces that maintain a coherence of the contour and move the point to a location of significant brightness changes, thereby forming the closed contour that bounds a region of a connected part of the human body, in which each point of the closed contour is considered as a particle that is subject to an action of two forces: a conditional attractive force acting between adjacent contour points, and a force proportional to a numerical estimate of a second derivative of an intensity of the image along the contour.

2. The method of claim 1, wherein a user freely chooses a viewing angle and a point of view to obtain the image.

3. The method of claim 1, wherein the method is used in an application installed on mobile devices without additional equipment.

4. The method of claim 1, wherein an optimization criterion for checking a match is composed of intensity differences between pairs of points in an external and an internal row taken with specific weight coefficients.

5. The method of claim 1, in which the flat object of known shape and size is an A4 sheet of paper.

6. The method according to claim 1, in which the particle dynamics method is used to create a closed contour of a foot and a lower leg.

7. The method according to claim 1, wherein an identification of the flat object image is performed using a method of searching for images of the flat object of known shape and size, the projection of the object, and the location and orientation of the camera, during which:
   multiple random resets of the camera position and orientation relative to the flat object of known shape and size are performed;
   a predicted image of the flat object of known shape and size is compared with the actual image;
   pairwise differences in brightness between points of an inner and outer rows of the template are calculated to compute a matching criterion.

8. The method according to claim 1, wherein the image photograph of the human body part is converted to a grayscale image.

9. The method according to claim 8, a Canny filter is applied to determine the boundaries of the objects in the photograph of the human body part, identifying points with the maximum brightness gradient, based on which an initial contour is constructed, which represents the closed contour, bounding the region of the connected part of the human body.

10. The method according to claim 1, in which conditional attractive forces are directed towards neighboring contour points and are computed based on a distance between the points, meaning that closer the points are to each other, the stronger the conditional attractive forces are.

11. The method according to claim 1, in which a force proportional to a numerical estimate of a second derivative of an intensity of the photograph along the contour is directed inward and increases the force if the contour is located in an area where the intensity of the photograph changes rapidly.

* * * * *